US009186086B2

(12) United States Patent
Lorenz et al.

(10) Patent No.: US 9,186,086 B2
(45) Date of Patent: Nov. 17, 2015

(54) SMALL TISSUE PROPERTY CHANGE DETECTION IN MAGNETIC RESONANCE GUIDED INTERVENTION

(71) Applicants: Christine H. Lorenz, Frederick, MD (US); Steven Michael Shea, Baltimore, MD (US)

(72) Inventors: Christine H. Lorenz, Frederick, MD (US); Steven Michael Shea, Baltimore, MD (US)

(73) Assignee: Siemens Aktiengesellschaft, Munich (DE)

( * ) Notice: Subject to any disclaimer, the term of this patent is extended or adjusted under 35 U.S.C. 154(b) by 472 days.

(21) Appl. No.: 13/680,314

(22) Filed: Nov. 19, 2012

(65) Prior Publication Data

US 2013/0137965 A1 May 30, 2013

Related U.S. Application Data

(60) Provisional application No. 61/564,996, filed on Nov. 30, 2011.

(51) Int. Cl.
*A61B 5/05* (2006.01)
*A61B 5/055* (2006.01)
*A61B 5/00* (2006.01)

(52) U.S. Cl.
CPC .............. *A61B 5/055* (2013.01); *A61B 5/0044* (2013.01)

(58) Field of Classification Search
CPC ........................................................ A61B 5/055
USPC ........................................................ 600/411
See application file for complete search history.

(56) References Cited

U.S. PATENT DOCUMENTS

| 2005/0215883 | A1* | 9/2005 | Hundley et al. ............... 600/410 |
| 2007/0003117 | A1* | 1/2007 | Wheeler et al. ............... 382/128 |
| 2009/0092304 | A1 | 4/2009 | Maier et al. |
| 2009/0096448 | A1 | 4/2009 | Meredith et al. |
| 2009/0290776 | A1 | 11/2009 | Sun et al. |

OTHER PUBLICATIONS

R. J. Kim et al., "Myocardial Gd-DTPA Kinetics Determine MRI Contrast Enhancement and Reflect the Extent and Severity of Myocardinal Injury After Acute Reperfused Infarction," Circulation, 15:94(12), pp. 3318-3326, Dec. 1996.
P. Kellman et al., "Motion-Corrected Free-Breathing Delayed Enhancement Imaging of Myocardial Infarction," Magnetic Resonance in Medicine, vol. 53(1), pp. 194-200, Jan. 2005.
C. McGann et al., "Dark Regions of No-Reflow on Late Gadolinium Enhancement Magnetic Resonance Imaging Result in Scar Formation After Atrial Fibrillation Ablation," Journal of the American College of Cardiology, vol. 58(2), pp. 177-185, Jul. 2011.
G. Vergara et al., "Real-time magnetic resonance imaging-guided radiofrequency atrial ablation and visualization of lesion formation at 3 Tesla," Heart Rhythm Society, 8(2), pp. 295-303, Feb. 2011.

(Continued)

*Primary Examiner* — Rajeev Siripurapu (57) ABSTRACT

Small tissue property change detection is provided for magnetic resonance (MR) guided intervention. T1 changes from before and after treatment are compared. The comparison identifies locations of possible change. The comparison is performed for different times, one before and one after a zero-crossing of a signal intensity time curve. Due to the characteristics of the T1 mapping, common locations from the different times will have reversed contrast. Clustering and this reversal are used to distinguish the treatment region from noise.

20 Claims, 4 Drawing Sheets

(56) References Cited

OTHER PUBLICATIONS

A. Arai, "Magnetic Resonance Imaging for Area at Risk, Myocardial Infarction, and Myocardial Salvage," Journal of Cardiovascular Pharmacology Therapeutics, Abstract, Sep.-Dec. 2011.

A. Zagrosek et al., "Cardiac Magnetic Resonance Monitors Reversible and Irreversible Myocardial Injury in Myocarditis," JACC Cardiovascular Imaging, 2(2), pp. 131-138, Feb. 2009.

H. Abdel-Aty et al., "T2 Weighted Cardiovascular Magnetic Resonance Imaging," Journal of Magnetic Resonance Imaging, 26(3), pp. 452-459, Sep. 2007.

S. Giri et al., "T2 quantification for improved detection of myocardial edema," Journal of Cardiovascular Magnetic Resonance, 11(56), pp. 1-13, Dec. 2009.

T. Grobner, "Gadolinium—a specific trigger for the development of nephrogenic fibrosing dermopathy and nephrogenic systemic fibrosis?," Nephrol Dial Transplant, 21, pp. 1104-1108, Oct. 2006.

D. C. Lock et al., "Time Saving in Measurement of NMR and EPR Relaxation Times," The Review of Scientific Instruments, 41(2), p. 250, Feb. 1970.

* cited by examiner

SMALL TISSUE PROPERTY CHANGE DETECTION IN MAGNETIC RESONANCE GUIDED INTERVENTION

RELATED APPLICATIONS

The present patent document claims the benefit of the filing date under 35 U.S.C. §119(e) of Provisional U.S. Patent Application Ser. No. 61/564,996, filed Nov. 30, 2011, which is hereby incorporated by reference.

BACKGROUND

The present embodiments relate to small tissue property change detection in magnetic resonance (MR) guided intervention.

MR imaging is used to detect change due to ablation. For example, liver, heart, muscle or kidney is thermally ablated, such as occurs in radio frequency, ultrasound, microwave, or cryogenic ablation therapy. The ablation may cause a change or difference in tissue properties resulting in MR T1 or T2 changes. If sufficiently large, the treated area appears differently in a T1 or T2 weighted image than surrounding, non-treated tissue. However, smaller treated areas may be more difficult to visually detect from a T1 or T2 weighted image. Moving and/or thin tissue structures may make detection of smaller treated areas more difficult. For example, T2-weighted MR sequences have relatively poor signal-to-noise ratio and are sensitive to motion.

For detection of RF ablation treatment areas in the heart, a T1-shortening contrast agent may be used. Using late-enhancement, areas in which residual contrast exists after a waiting period indicate damaged tissue. However, the wait period may be many minutes, making repeatability during an interventional procedure difficult. This difficulty is compounded by the effects of repeated administration of the contrast agents, which may not even be usable for patients with poor renal function.

BRIEF SUMMARY

By way of introduction, the preferred embodiments described below include methods, systems, and computer readable storage media for small tissue property change detection in magnetic resonance (MR) guided intervention. T1 changes from before and after treatment are compared. The comparison identifies locations of possible change. The comparison is performed for different time points, one before and one after a zero-crossing of a signal intensity time curve during inversion recovery. Due to the characteristics of the T1 mapping, common locations from the different times will have reversed contrast. Clustering and this reversal are used to distinguish the treatment region from noise.

In a first aspect, a method is provided for small tissue property change detection in magnetic resonance (MR) guided intervention. An MR scanner acquires a MR intensity curve of tissue response over time in response to an inversion pulse. A processor determines a first time before a zero crossing of the MR intensity curve and a second time after the zero crossing. First locations are identified from a comparison of an MR T1 map for the first time from before the MR guided intervention to an MR T1 map for the first time from after therapy in the MR guided intervention. Second locations are identified from a comparison of an MR T1 map for the second time from before the MR guided intervention to an MR T1 map for the second time from after therapy in the MR guided intervention. Tissue common to the first and second locations and with a reversed contrast for the first time as compared to the second time is located. An image indicating the common tissue is generated.

In a second aspect, a system is provided for small tissue property change detection in magnetic resonance (MR) guided intervention. A magnetic resonance (MR) scanner is configured to transmit inversion pulses and scan a patient at a pre-treatment baseline and at a post-treatment measurement. A processor is configured to identify time windows before and after a zero-crossing of intensity in response to at least one of the inversion pulse, identify regions with T1 changes from the baseline to the measure in each of the time windows, and locate one or more clusters from the regions where the one or more clusters have a reversed contrast for the time window before as compared to the time window after.

In a third aspect, a non-transitory computer readable storage medium has stored therein data representing instructions executable by a programmed processor for small tissue property change detection in magnetic resonance (MR) guided intervention. The storage medium includes instructions for detecting a location as a function of comparison from before and after therapy within periods before and after a zero crossing during inversion recovery where an opposite contrast is provided for the location from the period before than the period after the zero crossing, and outputting the location.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

T1 relaxation-derived information is compared to detect small changes in tissue properties during an MR guided therapeutic procedure, such as thermal ablation. The changes may be detected during the therapy. The regions affected by the therapy may be identified for confirmation and/or further intervention.

A combination of images with different T1 weightings, combined with comparison to baseline images, identifies areas that have undergone ablation or are otherwise scarred. No exogenous contrast agent is required. Relatively small areas (e.g., less than 2 mm) of tissue damage may be detected. Small changes in T1 may be detected by using different sources of information, such as T1 information in combination with a relative direction of offset between the baseline and the post-therapy measurements.

Figure 1:
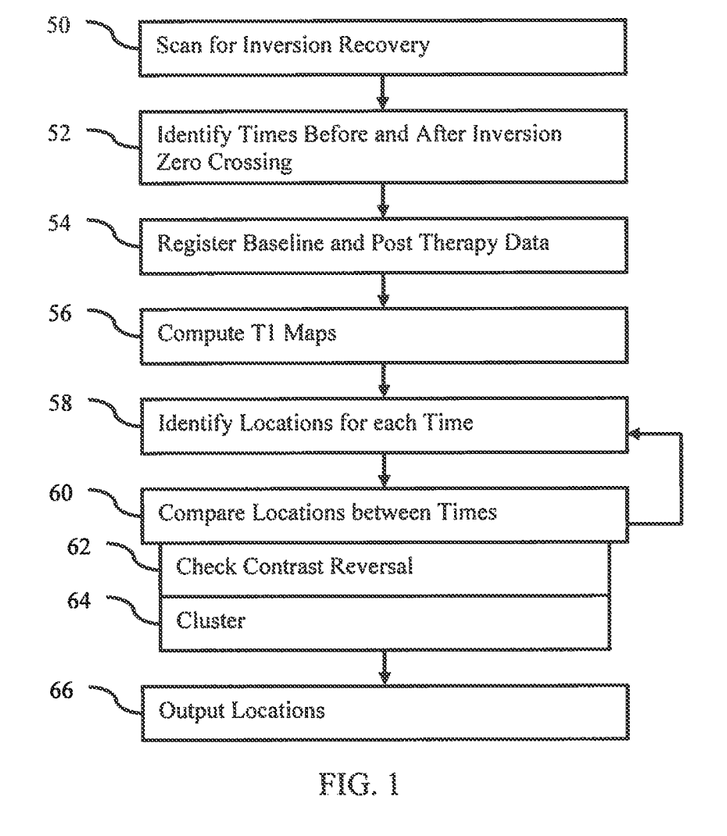
FIG. 1 is a flow chart diagram of an example embodiment of a method for small tissue property change detection in magnetic resonance (MR) guided intervention.

FIG. 1 shows a method for small tissue property change detection in MR guided intervention. A location is detected as a function of comparison from before and after therapy within periods before and after a zero crossing during inversion recovery. An opposite contrast is provided for the location from the period before than the period after the zero crossing, indicating detection of a treatment location rather than noise. Using comparison of T1 values, small clusters (e.g. 2 mm or less in any dimension) may be detected.

Figure 6:
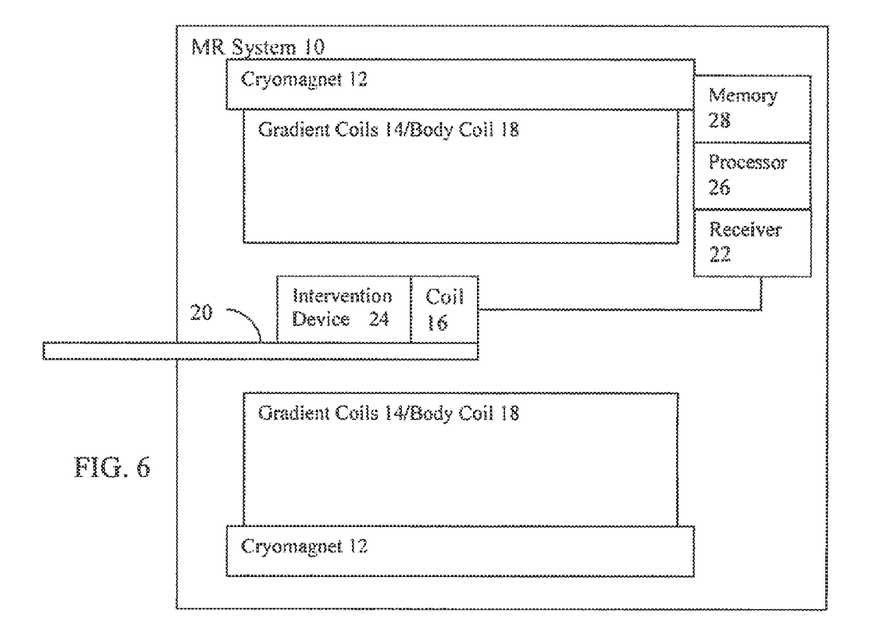
FIG. 6 is block diagram of one embodiment of a system for small tissue property change detection in MR guided intervention.

The method is performed by the MR system 10 of FIG. 6, a different system, a processor, or a computer. The acts are performed in the order shown, but other orders may be provided. For example, the registration of act 54 uses the T1 mapping, so is performed after act 56. As another example, the clustering of act 64 is performed as part of location identification 58 and prior to comparison between the times relative to the zero-crossing in act 60. In yet another example, the times relative to the zero crossing are identified after acquisition of the baseline data but before acquisition in act 50 of post-treatment data.

Additional, different, or fewer acts may be provided. For example, act 50 is not provided when the data is accessed from memory. As another example, registration of act 54, clustering of act 64, outputting of act 66, and/or combinations thereof are not provided. Acts associated with user input and/or sequencing of the MR scan may be provided.

In act 50, MR data is obtained. The MR data is obtained when the patient is scanned or obtained from memory where the patient was previously scanned.

The MR data represents anatomy of a patient. The patient is positioned relative to the MR scanner and scanned. The MR data represents a slice or volume of the patient. The MR data is a set of values for voxels representing a volume of the patient or pixels representing a plane.

A MR imaging system is used to scan within a patient. One or more transmitters produce an RF excitation field. A desired number of the transmitters are employed and connected through a corresponding number of transmit/receive switches to a corresponding number N of the coils in an RF coil array. The combined RF fields of the coil elements produce a prescribed $B_1$ field throughout the region of interest in the subject.

The signal produced by the subject in response to the RF excitation field is picked up by a coil array and applied to the inputs of the set of receive channels. The received signal is at or around the Larmor frequency. When the $B_1$ field is not being produced, the transmit/receive switches connect each of the receive channels to the respective coil elements. Signals produced by the excited spins in the subject are picked up and separately processed as k-space and/or object space data.

A scan sequence is performed to acquire the frames of MR data. The sequence is an inversion recovery scanning sequence. An inversion pulse is transmitted to flip the spin of the atoms relative to the main magnetic field. Additional scans are performed to map the recovery of the spins from the flipped condition to the stable condition caused by the main magnetic field. A series of frames of data representing the same region are acquired over time as the spin recovers. The sequence may be over one or more seconds. The sequence may use multiple inversion pulses and measure recovery at different times relative to the corresponding inversion pulse to provide frames over a time relative to the inversion. In one embodiment, a Look-Locker inversion recovery scan is performed.

This single type of MR acquisition is used for detection, reducing the acquisition time. The single type is inversion recovery. The inversion recovery allows extraction of T1 information. The longitudinal relaxation from inversion of the proton magnetization is measured. The T1 is a rate constant for the relaxation or recovery.

The scanning is performed at different times relative to the MR guided intervention. A series of frames of data are acquired prior to the MR guided intervention or prior to application of therapy during the MR guided intervention. Another series of frames are acquired after or during application of the therapy. Other series may be acquired throughout the therapy or at different points during the therapy. In alternative embodiments, one or more series of frames acquired during therapy are used as a baseline for one or more series of frames acquired at a later time, such as after completion or to verify completion of the therapy.

Other scanning may be performed. For example, the inversion recovery scanning is used to detect changes due to therapy. Other scanning may be used to detect the tools for applying the therapy, to detect tissue or anatomy, to detect function, or combinations thereof. Any types of MR scanning for guiding the intervention may be used.

Figure 2:
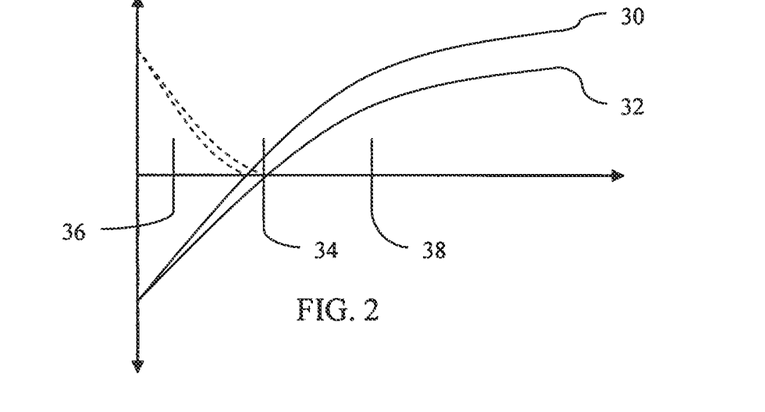
FIG. 2 is a graphical representation of example signal intensity curves during recovery from an inversion pulse.

Each series of frames during the recovery provides a sampling of an MR intensity curve of the tissue response over time to the inversion pulse. FIG. 2 shows two curves 30, 32. One curve 30 represents the inversion response of tissue after treatment. The other curve 32 represents the baseline response of the tissue prior to treatment. Due to the inversion, the intensity theoretically begins as negative values and exponentially recovers to positive values. The horizontal line represents time. The level of the horizontal line along the vertical intensity axis represents a zero level of the intensity.

The curves 30, 32 are extracted from the series of frames. The intensity in the temporal domain rather than k-space data is plotted as a function of time. The intensities from the frames at different times relative to the recovery are selected. These samples may be used as the curve or a curve may be fit to the samples.

The samples used for determining the curve are from a same location (e.g., voxel or pixel) within the patient. Alternatively, the intensity values from a plurality of locations in each frame are averaged and the average is used as the sample for that frame.

In act 52 of FIG. 1, at least two time points are determined relative to the zero crossing. Referring to FIG. 2, the zero crossing is of the curve 32, such as represented by the zero crossing 34. The zero-crossing 34 may be for the curve 30 from post therapy or calculated from both curves 30 and 32. The zero crossing 34 of the MR intensity curve during recovery or relaxation is located.

At least one time is selected from prior to the zero crossing 34, and at least one time is selected from after the zero crossing 34. For example, the times 36 and 38 are selected. The selection is of a time corresponding to a frame of data. The times 36, 38 are after the inversion pulse, but during the relaxation or recovery. Alternatively, the selection is of a time window or period associated with multiple frames of data. The window includes multiple times (e.g., samples associated with multiple frames in the series). A single or multiple T1 maps may be created for the selected time or time window, respectively.

Figure 3:
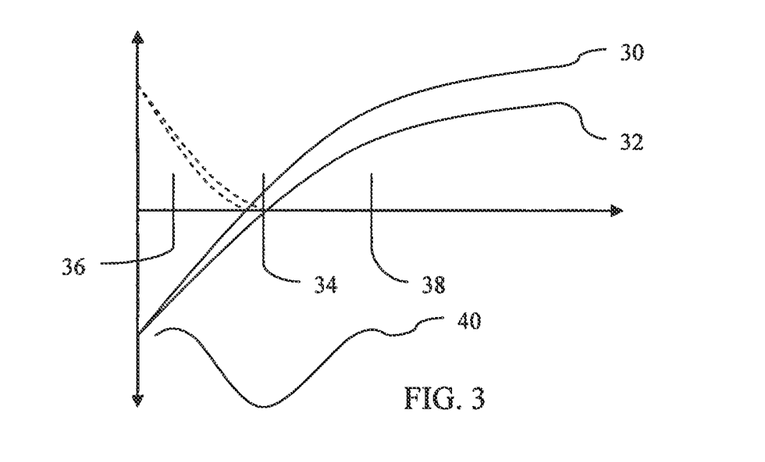
FIG. 3 is a graphical representation of the timing of a physiological cycle relative to the curves of FIG. 2.

The selection of the times 36, 38 is based on any criteria. For example, the times 36, 38 are selected to correspond to a same phase of a physiological cycle. The breathing, cardiac (e.g., heart), or other cycle may be used. FIG. 3 shows a cycle 40 relative to the time axis of the curves 30, 32. The recovery substantially (e.g., 75%) occurs over one cycle. Alternatively, the recovery may occur over multiple cycles. The times 36, 38 are selected to be at a same phase, such as the peak shown in FIG. 3. Any phase may be used.

In one embodiment, the selected phase corresponds to a time of lesser movement. For example, a phase corresponding to maximum expansion or contraction is used. In the cardiac cycle, the early systole and/or the late diastole is selected. The signal-to-noise ratio is likely higher during periods of less motion.

Another criteria is the signal-to-noise ratio. A tissue or patient specific threshold is used to determine times 36, 38 associated with better signal-to-noise. Even where motion does not occur, some frames may have better signal-to-noise ratio than other frames. The noise may be measured as a background signal from air or tissue spaced away from the region of intervention. The selection based on signal-to-noise ratio may be limited, such as requiring at least a predetermined separation in time from the zero crossing 34 and/or each other.

In one embodiment, a combination of phase and signal-to-noise ratio is used. Fuzzy logic, weighted average, or other selection may be used to select a time based on a combination of both phase of cyclic motion and the signal-to-noise ratio. In another approach, the cyclic motion is used to select a window. The time within the window is selected based on the signal-to-noise ratio.

Other criteria may additionally or alternatively be used for selecting the times 36, 38. For example, the selection is of a time a predetermined offset from the zero crossing, such as +/−0.5 seconds.

In act 54, the scans are registered. The baseline and any of the measures after the baseline are registered. The registration is of the different scans for the same time relative to the zero crossing. For example, the frame of data for the measure at the time before the zero crossing is registered with the frame of data for the baseline also at the time before the zero crossing. The frames of data from the different scans for the time after the zero crossing are spatially registered as well. Other scans from different times relative to the zero crossing may also be registered. The registration aligns the data so that the same location or locations are represented despite the scans occurring at different times (e.g., before, during, and/or after the therapy).

The data registered are the scan data. For example, the MR intensities are registered. Alternatively, act 56 is performed prior to registration. The resulting T1 maps are registered relative to each other.

The data is registered to spatially align the frames of data from different scans. The translation, orientation, and/or scale resulting in a greatest similarity or correlation is found. Alternatively or additionally, the registration may rely on sensors. The sensors indicate the position of the patient relative to the MR scanner. In another approach, fiducials are used.

Data may be used for registration. The registration may be based on the data in general. In other embodiments, the registration relies on segmentation of features and aligns based on the features. Features are detected. The features are mapped or labeled. The matching features from the different frames are determined, and a transformation relating the spatial positions is calculated. Other registration approaches may be used.

In one embodiment, the registration is a non-rigid registration. The relative spatial position of the locations represented by the data is not maintained, instead allowing for one or more degrees of freedom to warp the positions relative to each other to account for differences in spatial position. The registration may be rigid along one or more degrees of freedom. In one embodiment, the registration is non-rigid along all three spatial and all three rotational axes.

In one embodiment, elastic registration is used. The elastic registration algorithm may be based on the maximization of an intensity-based similarity metric. The metric may be selected from the group of local cross correlation and mutual information. The elastic registration algorithm may model the deformation as a smooth vector field. The deformation and its inverse may be estimated iteratively by maximizing an intensity-based similarity metric and are regularized using a low-pass filter.

In act 56, a T1 map is computed. An exponential fit is made of the curve of the intensity generated from single voxels or groups of voxels. The rate constant T1 is determined from the fit curve. The T1 map indicates the curve at the scan time. A T1 map is created for each of the frames of data or scans.

Figure 4A:
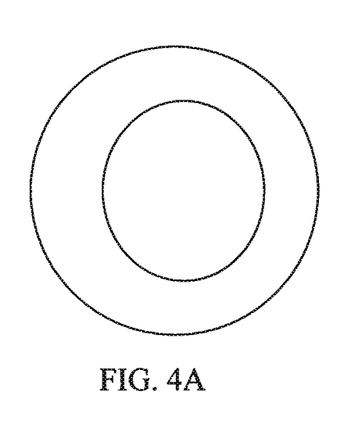
FIG. 4A is an example illustration of a baseline T1 map.
Figure 4B:
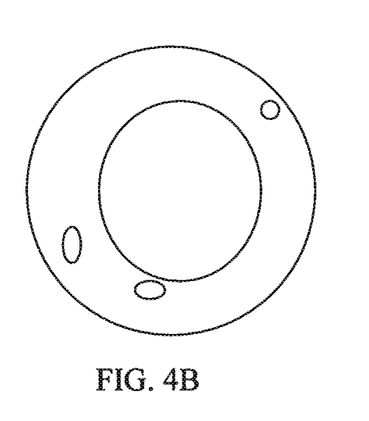
FIG. 4B is an example illustration of a T1 map measured after therapy.

In act 58, locations of possible change are determined from the T1 maps. Due to act 54, the relative locations represented by each T1 value are aligned. Since T1 maps are provided for different times relative to the therapy, any changes in the T1 characteristic represent a location of possible change due to therapy. The baseline is compared to one or more measures in a two or three-dimensional region. The example of FIGS. 4A and 4B are for scans both before or scans both after relative to the zero-crossing. Comparisons are made for each of the times 36, 38 relative to the zero crossing.

Any comparison function may be used. In one embodiment, the spatially aligned T1 data is subtracted. A difference between the T1 values is calculated. Using FIG. 2, the difference in intensity of the fit curves 30, 32 at the time 36, 38 relative to the zero crossing is determined. The baseline is subtracted from the measure, or vise versa. FIG. 4A shows an example T1 map for a baseline or before therapy. FIG. 4B shows the T1 map for the same region, but after therapy.

By differencing, the small elliptical and circular regions remain, but the other tissue is removed. The small elliptical and circular regions are representations of blobs, clusters, or other shapes.

Differences more likely to be associated with therapy related changes are identified. A threshold may be applied. Any differences with an absolute value greater than the threshold are maintained as possible change due to therapy. Clustering, edge detection, or other data processing may be used instead or in addition to thresholding to identify the locations of possible change due to therapy.

The identified locations from the different times relative to the zero crossing are used to increase the confidence in the locations being for changes due to therapy. In act 60, the locations between the times relative to the zero crossing are compared. Tissue common to both times are located. For example, if a change is found for one location for one time, but not at that location for the other time, then the location is ruled out or removed as a therapy-induced difference. As another example, if a difference is found for the same location in the comparison before the zero crossing and in the comparison after the zero crossing, the location remains as a possible location of a change due to therapy.

The commonality is determined by pixel, voxel, or point location. Each location is treated separately. The differences may be low pass filtered prior to determining commonality. Alternatively, the locations of possible change are clustered or combined. Commonality between combined locations is determined, such as providing an amount of overlap of locations.

Acts 62 and 64 represent further checks to identify the possible locations more likely being due to changes in T1 from therapy. Additional, different, or fewer checks may be provided. The clustering act 64 and contrast reversal check of act 62 may be used together. Any locations passing both criteria are locations showing the effects of therapy. In alternative embodiments, only one or the other of acts 62 and 64 is used.

In act 62, the difference from before the zero crossing is compared to the difference after the zero crossing. Referring to FIG. 2, dashed lines are shown for the period before the zero crossing. The dashed lines represent the actual signal. Since MR signals are not negative, the result is samples along the dashed lines for the baseline and post-treatment measure for before the zero crossing. Since the inversion pulse is used, these samples are known to be negative. The relative amplitude of the baseline and measure for the time 36 before the zero crossing is reversed as compared to the time 38 after. For before, the after treatment samples have a lesser value than the baseline. For after the zero crossing, the after treatment samples have a greater value than the baseline. As a result, the contrast for the time 36 is opposite or reversed from the time 38 after.

By differencing the baseline from the measure or the measure from the baseline the same for both before and after, positive values are provided for one comparison and negative values for another. By identifying different signs or reversed contrast, the locations are more likely associated with change due to therapy rather than noise. The characteristic of the recovery to an inverse pulse is used in combination with the nature of the MR measurement to locate change due to therapy and rule out noise.

In act 64, the common tissue is clustered. The locations adjacent each other or within a predetermined distance of each other are grouped together. The clustering identifies locations common to before and after the zero crossing that may be associated with a same treatment location. In alternative or additional embodiments, the clustering is performed on the difference information for each time 36, 38 independently of each other.

Any clustering may be used. For example, the locations are low pass filtered, such as with a Gaussian kernel. Region growing is applied to the filtered results. Any contiguously grouped locations are clustered together as one blob or region of possible therapy. Filtering, edge detection, or other image processing for clustering may be used.

The clusters are thresholded. Any threshold criteria may be used. For example, the shape of the cluster is used. The therapy is likely to result in particular shapes. The deviation of the cluster from an expected shape or library of expected shapes may be measured. Pattern matching or other process may be used for the thresholding. As another example, the variance in the edge of the cluster, cluster size, cluster size ratio (e.g., longest to shortest dimensions), and/or other characteristic may be used to select some and not other clusters as being for a change due to therapy.

In one embodiment, the identification of act 58 and location comparison of act 60 are repeated. Any number of repetitions may be performed. The repetitions are performed until a stable identification of the location of therapy is provided or until another criteria is met.

Each iteration is performed with one or more different settings. For example, one or more thresholds are altered for each iteration. The thresholds may be overly restrictive so that no locations are found in act 60. The thresholds are adjusted to be more inclusive. Alternatively, the thresholds may be overly inclusive. Too many clusters, clusters with borderline or non-qualifying shapes or other characteristics, or other indicia of overly inclusive thresholds may result. The repetition is performed with more restrictive threshold setting. Other settings than threshold may be altered, such as the pattern for matching or the algorithm used for identifying locations and/or comparing (e.g., use only clustering in act 64 or only checking in act 62 in one iteration but use the other in a next iteration).

In one embodiment, the shape of the cluster is used to control the number of iterations. Iterations are performed until one or more clusters with a desired shape are identified. In alternative embodiments, no repetition is used.

Figure 5:
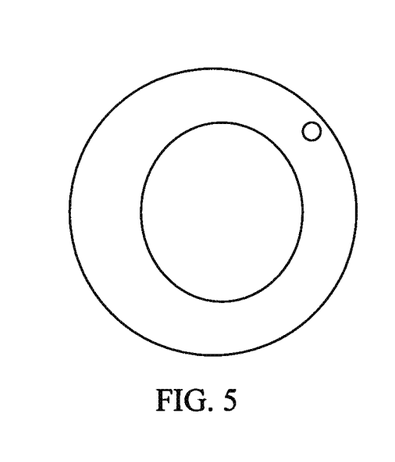
FIG. 5 is an example illustration of identification of a treatment region from comparison of T1 information.

FIG. 5 shows locating the therapy. After comparison and any iteration, the circular region is located. The elliptical regions are of the wrong shape, do not have contrast between the differences from pre and post zero crossing, or are otherwise removed as possible regions with change due to therapy. Any number of therapy regions with any of various shapes may be located as regions with change due to therapy.

The cluster, region, blob, or other group of locations representing the treatment location is of any size. Small regions, such less than 3 mm, less than 2 mm, or less than 1 mm in a longest dimension, may be located. Using the nature of the comparisons before and after the zero crossing and T1 measures, rapid (e.g., few minutes) identification of small regions with change due to therapy may be provided.

In act 66 of FIG. 1, the location of the therapy is output. The output may be coordinates, such as used for image processing, scanning, or directing therapy. The output may be an image. For example, an MR image from the scans acquired to detect the therapy location or another scan is generated. The location of the therapy is shown in the image. The location may be highlighted. Any form of additional highlighting may be used. For example, a graphic is overlaid at or near the location. As another example, intensities, brightness, color, or other modulation is performed differently for the location of the therapy than other locations. The data may be filtered, segmented, or otherwise processed for generating the image or images.

The image represents a two-dimensional slice, plane, or area within the patient. The images are of a standardized, arbitrary, scan, or other plane. The plane may be positioned to best view the location of therapy relative to the tissue being treated. Multi-planar reconstructions may be generated. In three-dimensional embodiments, the images are renderings. Any type of three-dimensional rendering may be used, such as projection or surface rendering.

FIG. 6 shows a system 10 for small tissue property change detection in magnetic resonance (MR) guided intervention. The system 10 includes a cryomagnet 12, gradient coils 14, whole body coil 18, local coil 16, patient bed 20, MR receiver 22, processor 26, and memory 28. Additional, different, or fewer components may be provided. For example, another local coil or surface coil is provided. As another example, no local coils 16 are used.

Other parts of the MR system are provided within a same housing, within a same room (e.g., within the radio frequency cabin), within a same facility, or connected remotely. The other parts of the MR portion may include cooling systems, pulse generation systems, image processing systems, and user interface systems. Any now known or later developed MR imaging system may be used with the modifications discussed herein. The location of the different components of the MR system is within or outside the RF cabin, such as the image processing, tomography, power generation, and user interface components being outside the RF cabin. Power cables, cooling lines, and communication cables connect the pulse generation, magnet control, and detection systems within the RF cabin with the components outside the RF cabin through a filter plate.

The processor 26 and memory 28 are part of a medical imaging system, such as the MR system 10. In one embodiment, the processor 26 and memory 28 are part of the MR receiver 22. Alternatively, the processor 26 and memory 28 are part of an archival and/or image processing system, such as associated with a medical records database workstation or server. In other embodiments, the processor 26 and memory 28 are a personal computer, such as desktop or laptop, a workstation, a server, a network, or combinations thereof. The processor 26 and memory 28 may be provided without other components for implementing the method.

The magnetic resonance scanner includes the cyromagnet 12, gradient coils 14, body coil 18, and any local coils 16. The cryomagnet 12, gradient coils 14, and body coil 18 are in the RF cabin, such as a room isolated by a Faraday cage. A tubular or laterally open examination subject bore encloses a field of view. A more open arrangement may be provided. The patient bed 20 (e.g., a patient gurney or table) supports an examination subject such as, for example, a patient with a local coil arrangement, including the coil 16. The patient bed 20 may be moved into the examination subject bore in order to generate images of the patient. Any local coils 16 are placed on, under, against, or in the patient. Received signals may be transmitted by the local coil arrangement to the MR receiver 22 via, for example, coaxial cable or radio link (e.g., via antennas) for localization.

In order to examine the patient, different magnetic fields are temporally and spatially coordinated with one another for application to the patient. The cyromagnet 12 generates a strong static main magnetic field $B_0$ in the range of, for example, 0.2 Tesla to 3 Tesla or more. The main magnetic field $B_0$ is approximately homogeneous in the field of view.

The gradient coils 14 radiate magnetic gradient fields in the course of a measurement in order to produce selective layer excitation and for spatial encoding of the measurement signal. The gradient coils 14 are controlled by a gradient coil control unit that, like the pulse generation unit, is connected to the pulse sequence control unit.

The nuclear spins of atomic nuclei of the patient are excited via magnetic radio-frequency excitation pulses that are transmitted via a radio-frequency antenna, shown in FIG. 1 in simplified form as a whole body coil 18, and/or possibly a local coil arrangement (e.g., local coil 16). Radio-frequency excitation pulses are generated, for example, by a pulse generation unit controlled by a pulse sequence control unit. After being amplified using a radio-frequency amplifier, the radio-frequency excitation pulses are routed to the body coil 18 and/or local coils 16. The body coil 18 is a single-part or includes multiple coils. The signals are at a given frequency band. For example, the MR frequency for a 3 Tesla system is about 123 MHz+/−500 KHz. Different center frequencies and/or bandwidths may be used.

Any pulse sequence may be used for scanning. In one embodiment, an inversion pulse is transmitted. After transmission, the patient is scanned to measure the inversion recovery or relaxation information. For example, the MR system 10 implements a Look-Locker sequence. The scanning occurs before therapy for a baseline measure and/or during therapy to identify any locations of change due to the therapy. Other sequences for T1-weighted measurement or T1 measurement may be used.

The signals emitted by the excited nuclear spins are received by the local coils 16 and/or the body coil 18. In the course of an MR measurement, the excited nuclei induce a voltage in the local coils 16. In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior) or under (posterior) or in the patient. The received signals are amplified by associated radio-frequency preamplifiers, transmitted in analog or digitized form, and processed further and digitized by the MR receiver 22. The recorded measured data is stored in digitized form as complex numeric values in a k-space matrix. An associated MR image of the examination subject may be reconstructed using a one or multidimensional Fourier transform from the k-space matrix populated with values.

The MR receiver 22 connects with the coils 16. The connection is wired (e.g., coaxial cable) or wireless. The connection is for data from the coils 16 to be transmitted to and received by the MR receiver 22. The data is K-space data. In response to an MR pulse, the coils 16 receive the K-space data and transmit the data to the MR receiver 22. Any pulse sequence may be used. Any spatial resolution may be provided, such as a spatial resolution of 0.78 mm.

The MR receiver 22 includes the processor 26 or another processor (e.g., digital signal processor, field programmable gate array, or application specific circuit for applying an inverse Fourier transform) for reconstructing the K-space data. The MR receiver 22 is configured by hardware or software to calculate data in the spatial domain from the K-space data. The processor 26 applies an inverse Fast Fourier transform to calculate the power spectrum of the projection data. The power spectrum provides intensity as a function of frequency. The frequency corresponds to space or distance. The MR data as acquired is a function of frequency and after applying inverse FT becomes a function of space. Any transform for reconstructing spatial data from the K-space data may be used.

The MR system 10 and MR scanner are configured by hardware and/or software to acquire frames of data. Scans are repeated to acquire frames of data representing the tissue response at different times relative to an inversion pulse. The series of scans are performed for a baseline before therapy and again at least once during or after therapy. T1-weighted information is acquired for different times for the baseline and the post therapy measure. The frames may be compared between the baseline and post therapy measure to find differences. The differences may be compared from before and after a zero crossing relative to inversion to distinguish locations associated with a change from therapy from locations associated with noise.

The intervention device 24 is a medical device for positioning within a patient. The intervention device 24 is a catheter, intercavity probe, needle, guide wire, or other medical device. The intervention device 24 is positioned in an orifice of the patient, such as through the mouth and into the esophagus. Alternatively, the intervention device 24 is positioned by surgical insertion through the skin of the patient, such as for minimally invasive surgery. In other embodiments, the intervention device 24 is inserted in an opening created as part of surgery, such as on an interoperative probe.

In one embodiment, the intervention device 24 is any now known or later developed catheter for intervention or other use within a patient. The catheter is sized and shaped for use in the circulatory system, such as having a diameter of 10 French or less, but a length of a foot or more. Alternatively, the catheter is sized and shaped for use at other locations in the body. The catheter is adapted for insertion within the patient, such as through a vessel or vein for extending into a heart chamber, body cavity, or other location within the patient. The catheter may include guide wires or be inserted through another previously positioned guide catheter. The catheter may include an electrode, scalpel, balloon, stent, imaging array, tube for injection, or other device for treatment of the patient.

The intervention device 24 is used to ablate. Electrodes, transducers, antenna, holder, or other device for radio frequency, acoustic, microwave, or cryogenic ablation is provided.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for distortion correction. The processor 26 is a single device or multiple devices operating in serial, parallel, or separately. The processor 26 may be a main processor of a computer, such as a laptop or desktop computer, or may be a processor for handling some tasks in a larger system, such as being part of the MR receiver 22 or MR imaging system 10. The processor 26 is configured by instructions, design, hardware, and/or software to perform the acts discussed herein, such as correcting for distortion using one or more connecting volumes.

The processor 26 is configured perform the method of FIG. 1 or another method. The processor 26 performs the acts, controls other components (e.g., MR system 10) to perform the acts, and/or acquires data to perform the acts.

In one embodiment, the processor 26 performs various data processing. For example, the processor 26 is configured to identify time windows before and after a zero-crossing of intensity in response to at least one inversion pulse. Regions with T1 changes from a baseline (pre-therapy) to a post therapy measure in each of the time windows are identified. Using an EKG or other signal indicative of a physiological cycle, the processor 26 may identify the windows based on being for a same phase of a physiological cycle. The processor 26 generates T1 maps for the baseline and measurement at the time windows. The T1 changes are identified from a comparison of the T1 maps separately for each of the time windows. The processor 26 locates one or more clusters from the regions where the one or more clusters have a reversed contrast for the time window before as compared to the time window after the zero crossing. Locations with the T1 changes that are in common locations for the different time windows and have contrast reversal are identified. Clustering may be used to rule out or to identify locations of therapy.

The memory 28 is a graphics processing memory, video random access memory, random access memory, system memory, cache memory, hard drive, optical media, magnetic media, flash drive, buffer, database, combinations thereof, or other now known or later developed memory device for storing data or video information. The memory 28 is part of an imaging system, part of a computer associated with the processor 26, part of a database, part of another system, a picture archival memory, or a standalone device.

The memory 28 stores K-space data, reconstructed data in the spatial domain (e.g., voxel values or intensities), T1 maps, coordinates, times, pulse sequences, registration information, comparison results, and/or other information used in image processing. As an alternative or in addition, the memory 28 stores protocols for scanning.

The memory 28 or other memory is alternatively or additionally a non-transitory computer readable storage medium storing data representing instructions executable by the programmed processor 26 for small tissue property change detection in magnetic resonance (MR) guided intervention. The instructions for implementing the processes, methods and/or techniques discussed herein are provided on non-transitory computer-readable storage media or memories, such as a cache, buffer, RAM, removable media, hard drive or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

A display may be provided for displaying an image or images generated for guiding intervention. The locations of therapeutic effect are highlighted for review by the medical professional. Determinations as to whether the intervention is complete or not may be made while the patient is sedated. The feedback, due to use of T1-weighted information without requiring other longer forms of scanning or contrast agent perfusion, may be within ten, five, or fewer minutes. The display is a monitor, LCD, projector, plasma display, CRT, printer, or other now known or later developed devise for outputting visual information. The display receives images, graphics, or other information from the processor 26 or memory 28.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for tissue property change detection in magnetic resonance (MR) guided intervention, the method comprising:
   acquiring, with an MR scanner, a MR intensity curve of tissue response over time in response to an inversion pulse;
   determining, with a processor, a first time before a zero crossing of the MR intensity curve and a second time after the zero crossing;
   identifying first locations from a comparison of an MR T1 map for the first time from before the MR guided intervention to an MR T1 map for the first time from after therapy in the MR guided intervention;
   identifying second locations from a comparison of an MR T1 map for the second time from before the MR guided intervention to an MR T1 map for the second time from after therapy in the MR guided intervention;

locating tissue common to the first and second locations and with a reversed contrast for the first time as compared to the second time; and
generating an image indicating the common tissue.

2. The method of claim 1 wherein acquiring the MR intensity curve comprises:
acquiring frames of data in a series of inversion recovery scanning before the MR guided intervention; and
sampling the intensities from the frames of data.

3. The method of claim 2 wherein acquiring the frames of data comprises acquiring with a Look-Locker scan.

4. The method of claim 1 wherein the MR T1 maps from before and after the MR guided intervention are selected from frames of data representing a slice of the tissue, the frames of data acquired with inversion recovery scanning sequences performed before and after the MR guided intervention.

5. The method of claim 1 wherein determining comprises determining the first and second times as being at a same phase of a physiological cycle, as corresponding to the tissue response having a signal-to-noise ratio above a threshold, or both at the same phase and the signal-to-noise ratio.

6. The method of claim 1 wherein determining comprises determining first and second periods, the first period including the first time, time to acquire the MR T1 map for the first time and time to acquire at least one additional MR T1 map, and the second period including the second time, time to acquire the MR T1 map for the second time, and time to acquire at least one additional MR T1 map.

7. The method of claim 1 wherein identifying the first and second locations comprises identifying the locations based on differences from before to after the MR guided intervention, the differences being above a threshold.

8. The method of claim 7 wherein locating comprises locating where the differences have a different sign from the first time as compared to the second time.

9. The method of claim 1 wherein locating comprises clustering the tissue common to the first and second locations and thresholding resulting clusters.

10. The method of claim 1 wherein generating the image comprises highlighting the tissue on a MR display of tissue of a patient.

11. The method of claim 1 further comprising non-rigidly registering the MR T1 maps for the first time and non-rigidly registering the MR T1 maps for the second time.

12. The method of claim 1 further comprising:
repeating the identifying and locating with different settings for a threshold, pattern matching, or algorithm used for the repetition of identifying and the locating; and
selecting the tissue common to the first and second locations from one of the repetitions as a function of a shape of a cluster of the tissue resulting from the one of the repetitions.

13. A system for tissue property change detection in magnetic resonance (MR) guided intervention, the system comprising:
a magnetic resonance (MR) scanner configured to transmit inversion pulses and scan a patient at a pre-treatment baseline and at a post-treatment measurement; and
a processor configured to identify time windows before and after a zero-crossing of intensity in response to at least one of the inversion pulses, identify regions with T1 changes from the baseline to the post-treatment measurement in each of the time windows, and locate one or more clusters from the regions where the one or more clusters have a reversed contrast for the time window before the zero-crossing as compared to the time window after the zero-crossing.

14. The system of claim 13 wherein the MR scanner is configured to perform Look-Locker sequences for the transmit and the scan.

15. The system of claim 13 wherein the processor is configured to identify the regions by generating T1 maps for the baseline and the post-treatment measurement at the time windows, the time windows being for a same phase of a physiological cycle, and identify the T1 changes from a comparison of the T1 maps for each of the time windows.

16. The system of claim 13 wherein the processor is configured to locate the one or more clusters by identifying locations with the T1 changes that are in common locations for the different time windows.

17. In a non-transitory computer readable storage medium having stored therein data representing instructions executable by a programmed processor for tissue property change detection in magnetic resonance (MR) guided intervention, the storage medium comprising instructions for:
comparing samples, for each of a plurality of locations in a patient, from before and after therapy within periods before and after a zero crossing during inversion recovery by a MR scanner where an opposite contrast is provided from the period before than the period after the zero crossing;
detecting at least one of the locations as having the tissue property change, the detection being a function of the comparing of the samples; and
indicating the at least one location in an image.

18. The non-transitory computer readable storage medium of claim 17 wherein the detecting comprises detecting using a single type of MR acquisition, the single type being inversion recovery, the comparison being of T1 values.

19. The non-transitory computer readable storage medium of claim 17 wherein the detecting comprises detecting the location as part of a cluster that is no larger than 2 mm in any dimension.

20. The non-transitory computer readable storage medium of claim 17 wherein detecting comprises detecting with the periods representing a same part of a cardiac cycle.

* * * * *